US006544175B1

(12) United States Patent
Newman

(10) Patent No.: US 6,544,175 B1
(45) Date of Patent: Apr. 8, 2003

(54) ULTRASOUND APPARATUS AND METHODS FOR DISPLAY OF A VOLUME USING INTERLACED DATA

(75) Inventor: Richard M. Newman, Stratham, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 26 days.

(21) Appl. No.: 09/663,480

(22) Filed: Sep. 15, 2000

(51) Int. Cl.[7] ................................................ A61B 8/00
(52) U.S. Cl. ...................................... 600/437; 600/443
(58) Field of Search ................................ 600/437, 438, 600/440–447, 450; 367/7, 11, 130; 73/625, 628; 128/916

(56) References Cited

U.S. PATENT DOCUMENTS

| 5,099,847 A | | 3/1992 | Powers et al. | |
|---|---|---|---|---|
| 5,570,691 A | * | 11/1996 | Wright et al. | 600/447 |
| 5,581,517 A | * | 12/1996 | Gee et al. | 367/11 |
| 5,720,291 A | * | 2/1998 | Schwartz | 128/916 |
| 6,099,471 A | * | 8/2000 | Torp et al. | 600/438 |

* cited by examiner

Primary Examiner—Marvin M. Lateef
Assistant Examiner—Ali M. Imam
(74) Attorney, Agent, or Firm—John Vodopia

(57) ABSTRACT

An ultrasound imaging system that produces a seemingly real-time display by obtaining ultrasound data in an interleaved manner. The system includes a transducer that outputs and receives ultrasonic signals and circuitry that causes the transducer to output the ultrasonic signals in a series of frames in an interleaved manner so as to isonify each of a plurality of portions of a subject matter at different times and forms an image based on the echoes from a plurality of frames.

18 Claims, 6 Drawing Sheets

ULTRASOUND APPARATUS AND METHODS FOR DISPLAY OF A VOLUME USING INTERLACED DATA

BACKGROUND OF THE INVENTION

The present invention relates to method and apparatus which creates an image for a display from interlaced ultrasound data, particularly ultrasound data acquired utilizing interlacing techniques including a spot volume method or a sparse volume method.

Ultrasound imaging has always involved a tradeoff between image quality and the image processing resources required to process the image to obtain the results desired by the user. While the rate at which data can be acquired is limited by physics (sound only travels so fast in the human body), the types of image processing that can be performed on the data is limited by the amount and quality of image processing resources that can be brought to bear upon the data. If real time imaging is desired, as it usually is, another limiting factor is the rate of data acquisition.

Ultrasound data is typically acquired in frames, each frame representing a complete sweep of an ultrasound beam across the face of a transducer. In the case of a 1-D transducer, a sweep is typically 2-D pie-shaped. For a 2-D transducer, the sweep can be of a multitude of defined (and undefined for that matter) shape, but for purposes of discussion herein, it will be assumed to be a sweep, originating at the transducer and extending over a 2-dimensional rectangular surface, parallel with the face of the probe, at some distance from the probe. Such a sweep can, for the purposes of discussion, be thought of as being pyramidal in shape.

The amount of ultrasound data produced by a 2-D probe can be difficult to receive and process. It is estimated that to process a relatively large volume (60°×60°) of ultrasound data in real time, a beamformer capable with 16× parallelism is required. Such a beamformer would be extraordinarily expensive, especially in a market where the acceptable cost of ultrasound systems is rapidly reducing. The typically solution has been to use a lower cost beamformer with a reduced the frame rate. Thus, there currently exists a tradeoff between the benefit of 3-D ultrasound imaging and image quality due to lack of processing resources.

The present inventors have recognized a need for an ultrasound system that is capable of delivering at least the illusion of a real-time image, thereby increasing the quality of the perceived image, while utilizing standard processing resources, including cost effective beamformers. Further, the present inventors have recognized a need for a 3-D solution that can be added, as an upgrade, to existing 2-D systems.

SUMMARY OF THE INVENTION

An ultrasound imaging system that produces a seemingly real-time display by obtaining ultrasound data in an interleaved manner. The system includes a transducer that outputs and receives ultrasonic signals and circuitry that causes the transducer to output the ultrasonic signals in a series of frames in an interleaved manner so as to isonify each of a plurality of portions of a subject matter at different times and forms an image based on the echoes from a plurality of frames.

One example of interleaving is the spot volume method in which the subject matter is divided in to areas, with each area being scanned at different times. A second example of interleaving is the sparse volume method in which the subject matter is scanned with sparse line spacing, e.g. scanning every other line, every second line, every third line, etc. . . . On subsequent scans, the remaining lines are scanned.

An image is constructed using several frames of data, with only the portion actually being scanned being updated with actual data for each display frame. For most imaging tasks, such interleaving will provide an adequate illusion of real-time imaging. If necessary alignment processing or interpolation processing can be used to improve (or at least smooth) image quality.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
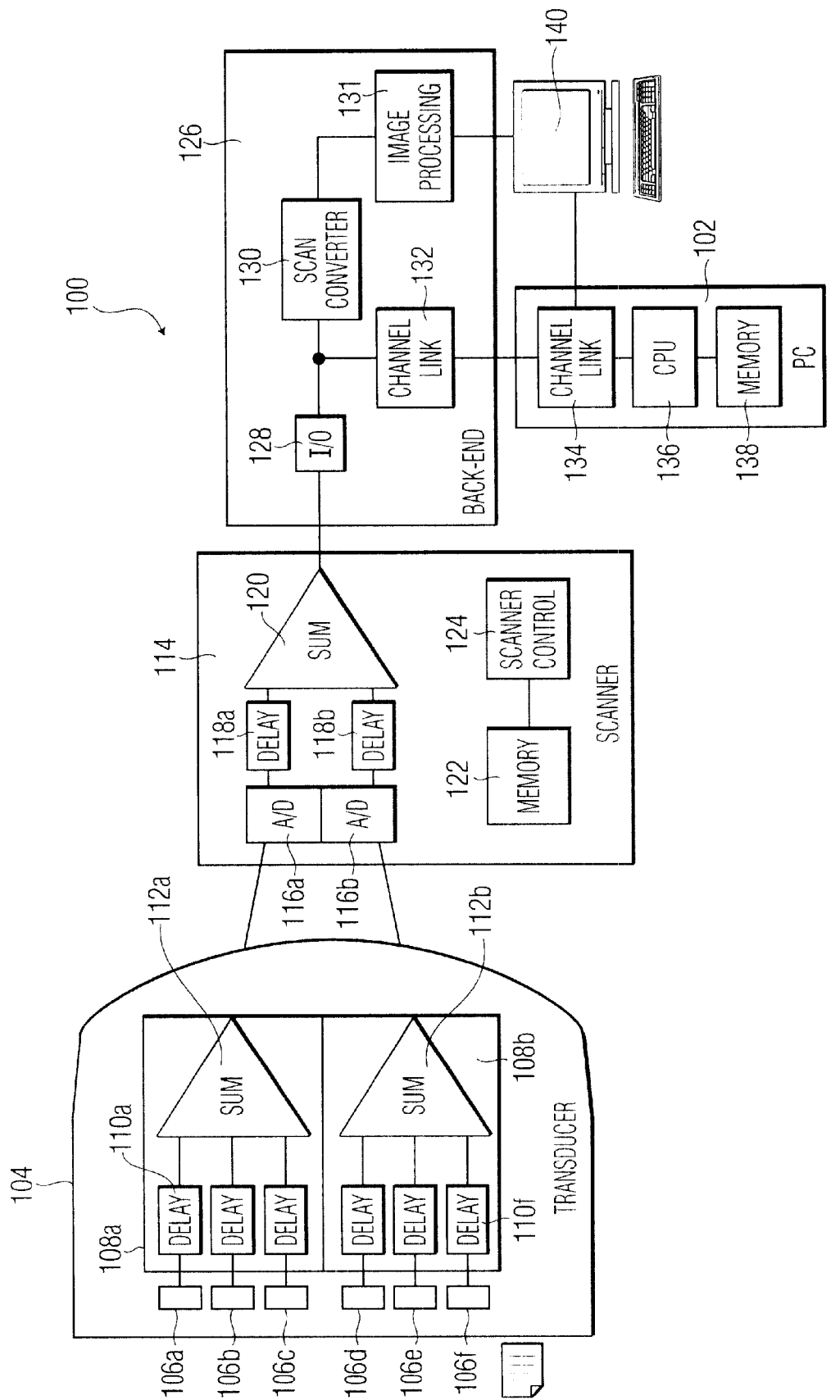
FIG. 1 is a block diagram of an ultrasound imaging system in accordance with preferred embodiments of the present invention.

Reference will now be made in detail to the present preferred embodiments of the present invention, examples of which are illustrated in the accompanying drawings, wherein like reference numerals refer to like elements throughout.

The detailed description which follows is presented in terms of routines and symbolic representations of operations of data bits within a memory, associated processors, and possibly networks, and network devices. These descriptions and representations are the means used by those skilled in the art effectively convey the substance of their work to others skilled in the art. A routine is here, and generally, conceived to be a self-consistent sequence of steps or actions leading to a desired result. Thus, the term "routine" is generally used to refer to a series of operations performed by a processor, be it a central processing unit of an ultrasound system, or a secondary processing unit of such an ultrasound system, and as such, encompasses such terms of art as "program," "objects," "functions," "subroutines," and "procedures."

In general, the sequence of steps in the routines require physical manipulation of physical quantities. Usually, though not necessarily, these quantities take the form of electrical or magnetic signals capable of being stored, transferred, combined, compared or otherwise manipulated. Those of ordinary skill in the art conveniently refer to these signals as "bits", "values","elements", "symbols", "characters", "images", "terms", "numbers", or the like. It should be recognized that these and similar terms are to be associated with the appropriate physical quantities and are merely convenient labels applied to these quantities.

In the present case, the routines and operations are machine operations to be performed in conjunction with human operators. Useful machines for performing the operations of the present invention include the AGILENT TECHNOLOGIES SONOS 5500 and other similar devices. In general, the present invention relates to method steps, software, and associated hardware including computer readable medium, configured to store and/or process electrical or other physical signals to generate other desired physical signals.

The apparatus set forth in the present application is preferably specifically constructed for the required purpose, i.e. ultrasound imaging, but the methods recited herein may operate on a general purpose computer or other network device selectively activated or reconfigured by a routine stored in the computer and interface with the necessary ultrasound imaging equipment. The procedures presented herein are not inherently related to any particular ultrasonic system, computer or other apparatus. In particular, various machines may be used with routines in accordance with the teachings herein, or it may prove more convenient to construct more specialized apparatus to perform the required method steps. In certain circumstances, when it is desirable that a piece of hardware possess certain characteristics, these characteristics are described more fully in the following text. The required structures for a variety of these machines may appear in the description given below. Devices which may perform the functions of the present invention include ultrasound systems by such companies as AGILENT TECHNOLOGIES, ADVANCED TECHNOLOGY LABORATORIES, INC., as well as other manufacturers of ultrasound equipment.

With respect to the software described herein, those of ordinary skill in the art will recognize that there exists a variety of platforms and languages for creating software for performing the procedures outlined herein. Those of ordinary skill in the art also recognize that the choice of the exact platform and language is often dictated by the specifics of the actual system constructed, such that what may work for one type of system may not be efficient on another system.

FIG. 1 is a block diagram of an ultrasound imaging system 100 in accordance with preferred embodiments of the present invention. It will be appreciated by those of ordinary skill in the relevant arts that the ultrasound imaging system 100, as illustrated in FIG. 1, and the operation thereof as described hereinafter is intended to be generally representative such systems and that any particular system may differ significantly from that shown in FIG. 1, particularly in the details of construction and operation of such system. As such, the ultrasound imaging system 100 is to be regarded as illustrative and exemplary and not limiting as regards the invention described herein or the claims attached hereto. For example, the ultrasound system 100 utilizes a standard personal computer ("PC") 102, to act as a 3-D image processor, as discussed herein below, but application specific processors, such as ASICs, could be utilized and the image processing functions integrated in the main housing (not shown) of the ultrasound system 100. As another alternative, a central processor of an appropriately configured ultrasound system could be utilized to perform the image processing function.

The ultrasound system 100 has a transducer assembly 104 that is preferably configured as a two-dimensional array.

That is, a 2-D array of elements 106 is provided for sending and receiving ultrasonic signals. In the Example shown in FIG. 1, only elements 106*a* through 106*f* are illustrated, but those of ordinary skill in the art will recognize that any number of elements can be utilized, for example a 50×50 element array. The transducer 104 is preferably configured for partial beamforming using a series of ASICs 108, although those of ordinary skill in the art will recognize that alterative configurations are possible, for example full beamforming in either the transducer 104 or in the main housing of the ultrasound system 100. Two ASICs 108*a* and 108*b* are illustrated, corresponding to elements 106*a–f*. In the example shown each ASIC 108n is connected to three (3) elements although those of ordinary skill in the art will recognize that other designs are possible. For example, depending on the level of integration, 5, 15, or 25 elements could be connected to each ASIC 108n. Each ASIC 108n is provided with a plurality of delay circuits 110n (one for each element connected to the ASIC 108n) that delay the output of a connected element 106n by a programable amount in a known manner so as to focus and steer acoustic beams. A sum circuit 112n combines the output of the delay circuits 110n in each ASIC 108n.

The output of each ASIC 108n is provided to a scanner 114, preferably located in a main housing of the ultrasound system 100, to complete beamforming. The output of each sum circuit 112n from each ASIC 108n is first A/D converted by a corresponding A/D converter 116n. The converted output of each sum circuit 112n is then delayed by a corresponding delay circuit 118n and subsequently summed with other delayed converted outputs by a sum circuit 120. Circuitry to perform image detection (not shown) is provided, perhaps as part of the sum circuit 120 to produce echo data by performing an image detecting procedure on the summed signal.

A scanner control circuit 124 controls the timing and operation of the scanner 114 and transducer 104 using delay coefficients stored in a memory 122.

Those of ordinary skill in the art will recognize that the illustrated transducer 104 and scanner 114 are illustrated as being configured to receive ultrasonic echoes. However, the transducer 104 and scanner 114 are similarly configured during transmit using similar delay coefficients.

The output of the scanner 114 is provided to a back-end 126, usually provided in the main housing, via an I/O 128 for subsequent signal processing. In the preferred embodiment, the back-end 126 perform 2-D signal processing, while the PC 102 performs 3-D image processing. The configuration shown in FIG. 1 enables the upgrade of prior 2-D based ultrasound systems to handle 3-D data. The back-end 126 is provided with a scan converter 130 which converts the 2-D scan data into X-Y space. Subsequent to scan conversion an image processing unit 131 is provided that can be configured to perform a variety of 2-D image enhancement processes, such as color flow, Doppler, ect. . . , to create image data for display on a monitor 140. While the present invention can be practiced on 2-D data, the preferred embodiment is directed toward the processing of 3-D data, such that further discussion of the various types of 2-D image processing will be dispensed with so as not to obscure the preferred embodiment.

An channel link transmitter 132 transfers the echo data received by the back-end 126 to the PC 102 which receives the echo data via a channel link receiver 134. The channel link can be formed using chip pairs, available from a variety of manufacturers, that conform to the Low Voltage Differential Signaling standard. As shown, the data transferred to the PC 102 is preferably obtained from a data bus in the back end 126 prior to scan-conversion.

A CPU 136 performs computational tasks, including 3-D scan conversion (into X-Y-Z space) under the control of programs stored in memory 138. The CPU 136 creates display data which forms the basis for subsequent output to a monitor 140 (via, for example, an AGP video card (not shown)). One example of an image process performed by the PC 102 is 3-D rendering and 3-D data manipulation, preferably with the assistance of an expansion card such as the VOLUMEPRO series of cards supplied by MITSUBISHI. 3-D rendering, as is known to those of ordinary skill in the art, turns 3-D data into display data suitable for display on a 2-D screen. Further, in accordance with the preferred embodiment of the present invention, the PC 102 performs image construction from a series of interlaced sub-volumes produced during a series of sub-volume sweeps. This can be performed by creating a matrix of data in the memory 138 to hold the entire volume of data and updating the matrix each frame with data obtained during that frame.

The present invention is particularly suited to two types of imaging: breath-hold and real-time. Breath-hold imaging is particularly suited to cardiac imaging, while real-time imaging is more general in nature. In breath-hold, a patient is requested to hold his breath for a short duration, say 4–20 heart beats (2 to 15 seconds) while echo data is collected. The purpose of having the patient hold his or her breath is to attempt to eliminate the movement of the body (and in particular the heart) caused by the motions of breathing. The goal of breath-hold imaging is to produce a short motion picture of a couple of beats of a patient's heart. Real-time imaging presents a real-time, or more correctly near real-time, view of a region of interest within a patient's body. The real-time view can be analyzed during acquisition and/or recorded for later analysis.

Figure 2:
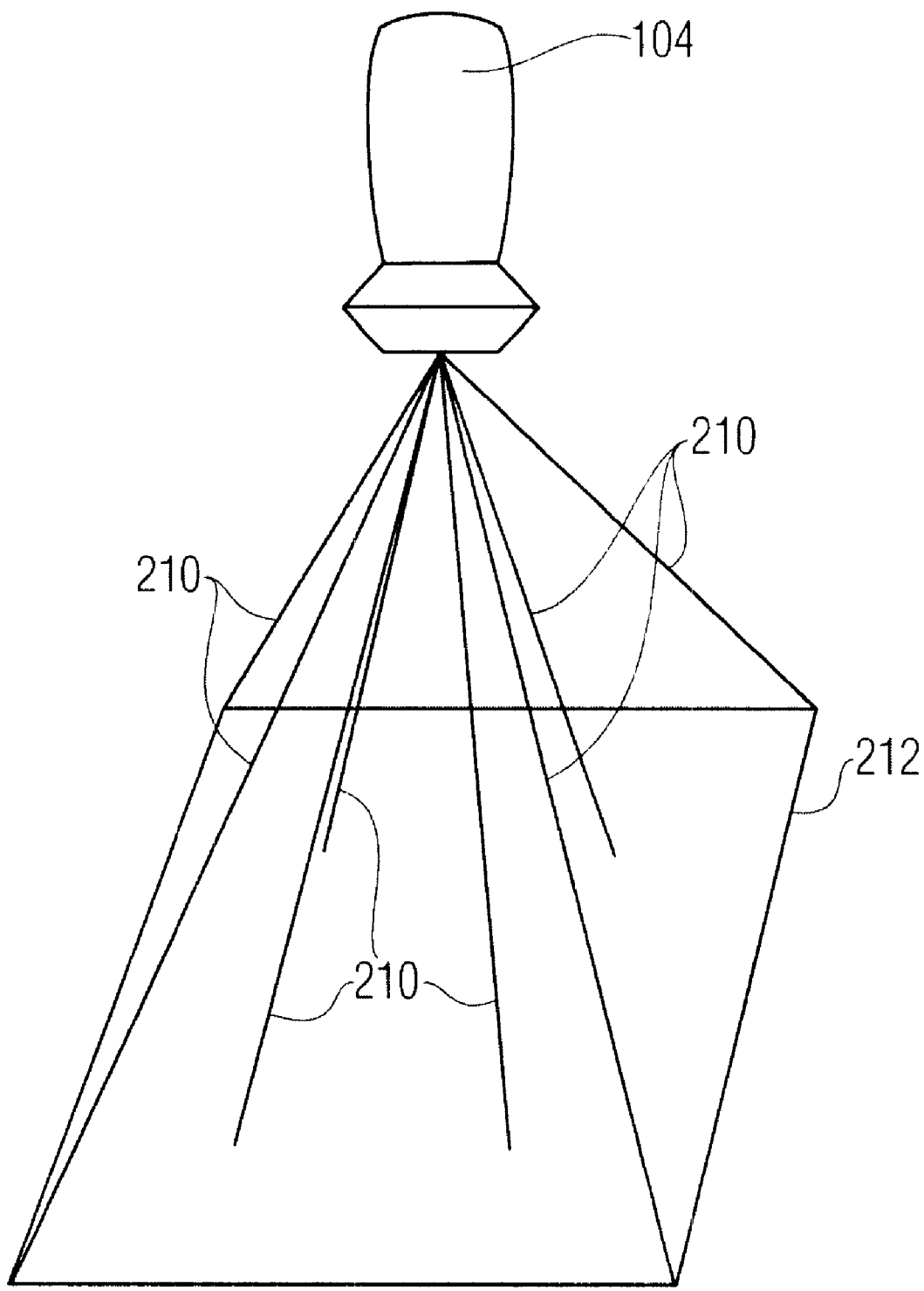
FIG. 2 is a diagram of a 2-D transducer performing a sweep.
Figure 3A:
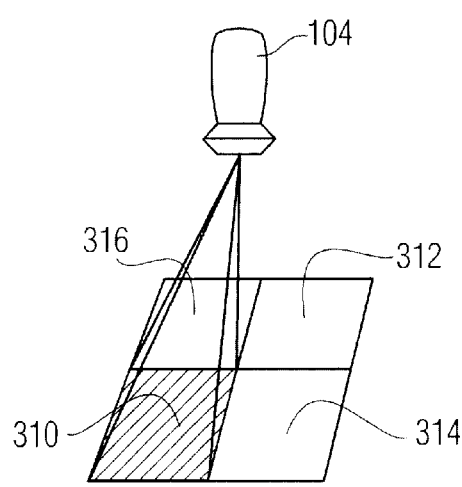
FIGS. 3a through 3e are diagrams of a transducer in operation in accordance with a first preferred embodiment of the present invention.
Figure 3B:
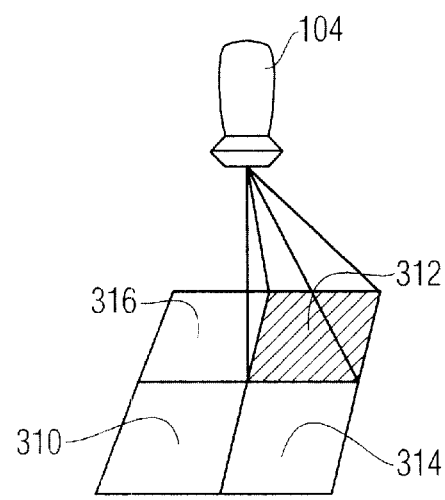
Figure 3C:
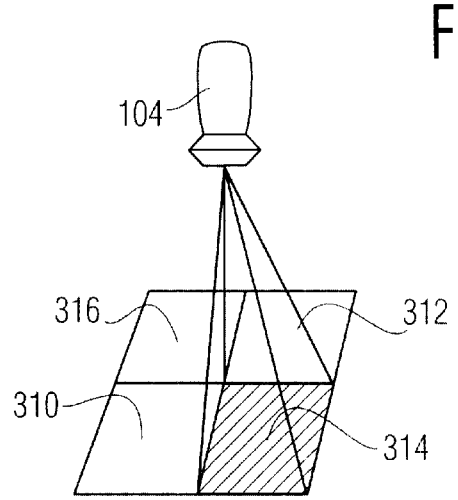
Figure 3D:
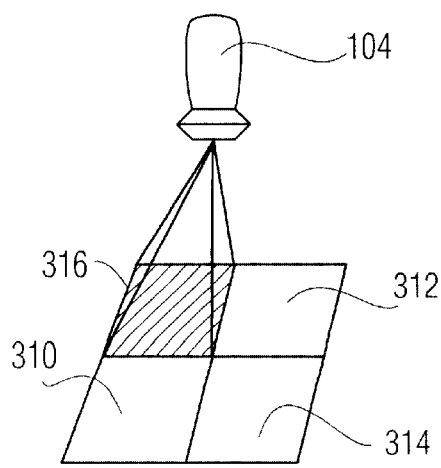
Figure 3E:
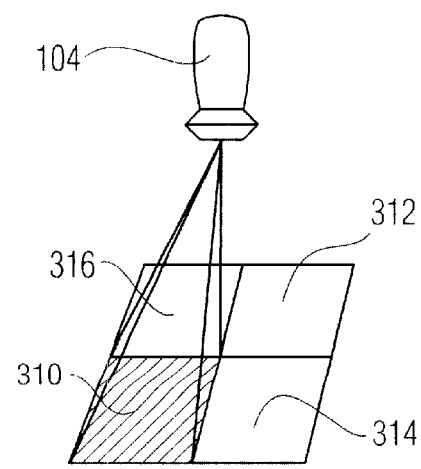

FIG. 2 is a diagram of a 2-D transducer performing a sweep. The transducer 104 emits a series of scan lines 210 (only a small percentage of which are depicted) over a target area 212. In general, the transducer 104 has a phased 2-D array of piezoelectric elements that can steer an ultrasonic beam along azimuth and elevation directions, as well as focus along the depth direction, providing the ability to scan a volume. FIG. 2 and the remaining Figures illustrate the scanning of a planar rectangular area, but those of ordinary skill in the art will recognize that this is for explanatory purposes only. In fact, most 2-D array systems are capable of scanning a plurality of 1-D, 2-D and 3-D shapes. Further in the remaining Figures, the depiction of scan lines, both in number and form, has been simplified for explanatory purposes.

FIGS. 3*a* through 3*e* are diagrams of a transducer in operation in accordance with a first preferred embodiment of the present invention. The present invention is directed toward causing the transducer 104 to output ultrasonic scan lines in an interleaved manner so as to sequentially isonify different portions (also referred to as sub-regions or sub-volumes) of the subject matter to be imaged and forming (or "reconstructing") an image of the entire volume using a series of frames. In a preferred embodiment, when imaging the heart, a different sub-region is imaged each beat (or cardiac cycle) of the heart (triggered by, for example, an ECG lead). Thus, for any given cardiac cycle of the heart a sequence of frames are taken of a specified sub-volume. Assuming that four (4) sub-regions are defined, a virtual moving image of a complete cardiac cycle of the heat can be constructed after four cycles. Contrary to expectations, in actual tests of such a system/method using the breath-hold method, surprisingly good images have been obtained.

In general, each heart beat is much like the prior (and subsequent) heart beat, thus, by splicing (e.g. interleaving) together a series of images taken from different heart beats, a complete rendition of a patient's heart beat can be displayed. Such reconstruction is particularly suited for breath-hold imaging of a heart where the quick movements of the heart cause significant changes from frame to frame. Accordingly, it is preferable to collect a series of frames of data for a sub-volume over a cardiac cycle, and switch to another sub-volumes on the subsequent cycles. It has been found that this progression, at least for cardiac imaging, avoids discontinuities that would occur if the sub-volume being imaged was switched each frame. However, for slower moving tissue/fluids it is believed that switching sub-volumes each frame would provide a usable image.

To be able to rapidly switch between scanning sub-volumes in a full volume scan, the coefficients in the memory 122 need to be modified. Preferably, the present invention provides a practical full-volume scanner having a 60×60 degree frustum composed of 4 successive sub-volumes of approximately 60×15 degrees each, each sub-volume scanned at 1 degree resolution both laterally and in elevation, using 4× parallel beamforming, each sub-volume producing a total of about 900 receive lines. To make the system practical, it is desirable to switch between scanning sub-volumes within about a 15 msec period at the end of a sequence of frames shot during each heartbeat. One method is to reuse coefficient line numbers and memory for each sub-volume, so at the time of switching from one sub-volume scan to the next, coefficients must be calculated and written (over the previous ones). However, as opposed to the desired 15 msec for the switch, such recalculation could consume as much as 5 seconds, requiring the patient to hold his/her breath for an excessive period of time (breath-hold) or causing large discontinuities (real-time). Preferably, the number of coefficients in the memory 122 is increased (compared to current systems) for both transmit and receive, with each coefficient being pre-calculated for all the scan lines of all the sub-volumes and thus achieve the desired 15 msec switch by just changing coefficient line number indexing in a Frame Table. This minimizes the need for long duration breath-holds and provides superior real-time images.

FIGS. 3*a* through 3*e* show a sequence of frames obtained using a spot volume method. During imaging (breath-hold or real-time), a different dense sub-volume (for example a 30° by 30° portion with 1° line spacing) of the subject matter to be imaged is acquired each cardiac cycle. The number of frames acquired each cycle is dependent on the frame rate of the ultrasound system and the patient's heart rate. Consecutive frames of sub-volumes are combined to produce a complete dense volume. In breath-hold imaging, a predetermined number of cardiac cycles are imaged and reconstruction can be performed to produce a motion picture of one or more cardiac cycles. Re-construction can be performed off line if desired. In real-time imaging, reconstruction is performed concurrently, for example by filling an array with data which is read to produce an image. As the cycle repeats, new sub-volumes overwrite previous sub-volumes to produce a full volume that appears to update continuously.

Looking at FIGS. 3*a* through 3*e* a series of frames are portrayed. In this instance, the subject matter to be imaged is divided into four (4) quadrants: 310–316. In the example shown in FIGS. 3*a*–3*e*, a diagonal pattern is used to form subsequent scans. Specifically, in a first cardiac cycle the lower left quadrant 310 is scanned and in subsequent cycles the upper right quadrant 312, the lower right quadrant 314 and the upper left quadrant 316 are scanned in order. In a fifth (5th) cycle, the lower left quadrant 310 is re-scanned, with the new data overwriting the old data. Those of ordinary skill in the art will recognize that there exist a variety of different ways to subdivide the subject matter to be imaged into scanning patterns, any of which may produce equivalent results to the quadrants shown in FIGS. 3a–3e. For example, the area to be imaged could be divided into vertical or horizontal slices.

Alternatively, for imaging of a 3-D surface, the volume could be split into cubes, rectangular slices or some other shape. Those of ordinary skill in the art will also recognize that FIGS. 3a–3e are highly simplified for the purposes of explanation.

In the context of FIG. 1, the ultrasound data produced by the interleaved scan shown in FIGS. 3a–3e, is stored in a multi-dimensional array, corresponding to the subject matter to be imaged, in the memory 138 (after having been scan converted by the CPU 136). The data in the array will be updated with each subsequent scan. In the example shown in FIGS. 3a–3e, after four (4) cycles (and each subsequent cycle), a complete array of data is available for rendering and display. Those of ordinary skill in the art will recognize that any number of division can be used to define sub-volumes, FIGS. 3a–3e illustrate the use of four sub-volumes, however, two (2), three (3), five (5), six (6) etc. . . sub-volumes could be used.

If the probe is held relatively still during data acquisition, such as with breath-hold imaging, the spatial alignment will be sufficient without performing any alignment correction. However, spatial alignment processing, as is known to those of ordinary skill in the rendering art, can be implemented by adding the appropriate functions to the memory 138. Further, it is anticipated that changes in the heart rate will be gradual enough so as not to require any temporal correction between the acquisition of sub-volumes, however, in the case of an arrhythmia (or other rapid change in heart rate), it may be necessary to provide interpolated data for the sub-volumes. This would involve the use of an interpolation process stored in the memory 138, that for example calculates averages over time and/or space and updates data in the static quadrants for any given frame of display data.

Figure 4A:
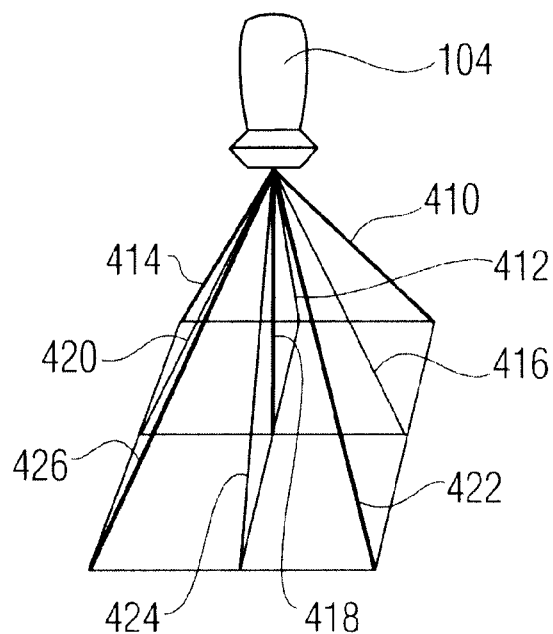
FIGS. 4a and 4b are diagrams of a transducer in operation in accordance with a second preferred embodiment of the present invention.
Figure 4B:
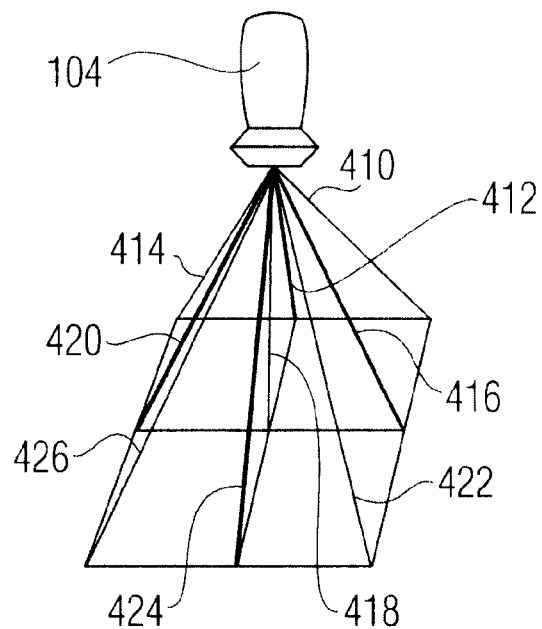

FIGS. 4a and 4b are diagrams of a transducer in operation in accordance with a second preferred embodiment of the present invention. FIGS. 4a and 4b show a sequence of frames obtained using a sparse volume method. During live imaging different scan lines covering the whole subject matter to be imaged are acquired each cardiac cycle. For example, in a 60°×60° volume, scanning alternative frames using interleaved 2× normal line spacing. Consecutive sequences of frames are combined to produce a complete dense volume. As the cycle repeats, new data overwrite previous data to produce a full volume that appears to update continuously.

Looking at FIG. 4a, in a first cardiac cycle, the transmitter 116 causes the transducer 104 to emit a first series of frames comprised of a first set of scan lines 410, 414, 418, 422, and 426 (shown in bold). The data from the first series of frames is loaded into the appropriate locations in the memory 138. Subsequently, in a second cardiac cycle shown in FIG. 4b, the transmitter 116 causes the transducer 104 to emit a second series of frames comprising a second set of scan lines 412, 416, 420, and 424 (shown in bold). The data from the second series of frames is loaded into the appropriate locations in the memory 138. After two series have been stored in the memory 138 (and for each subsequent series), a complete set of ultrasound data has been produced and a video controller (not shown) can retrieve and display the ultrasound data. Those of ordinary skill in the art will recognize that FIGS. 4a and 4b are highly simplified for the purposes of explanation. In fact, hundreds of scan lines would be used to image the region shown. Further, those of ordinary skill in the art will recognize that more than two (2) series could be used to construct an image, for example three (3) or four (4) might also produce acceptable results depending on the region being imaged.

Figure 5A:
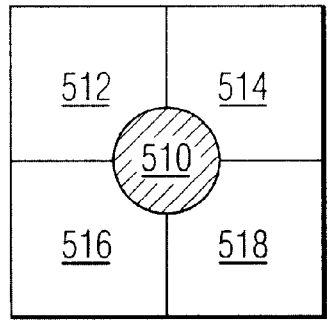
FIGS. 5a through 5i are diagrams of a transducer in operation in accordance with a third preferred embodiment of the present invention.
Figure 5B:
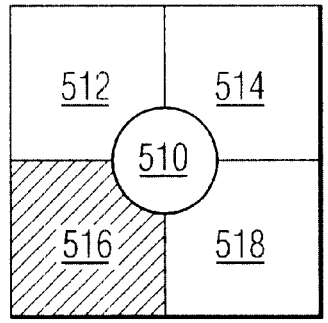
Figure 5C:
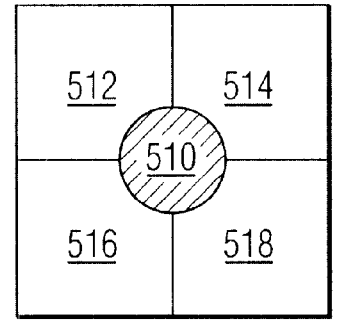
Figure 5D:
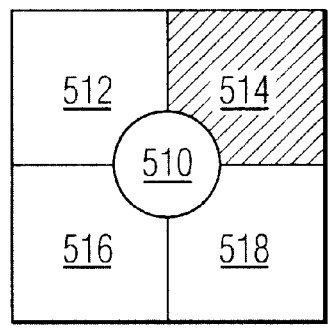
Figure 5E:
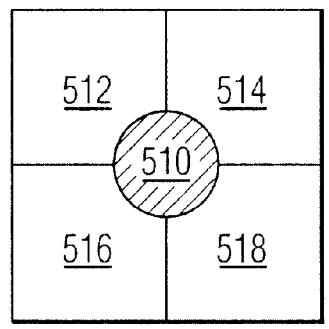
Figure 5F:
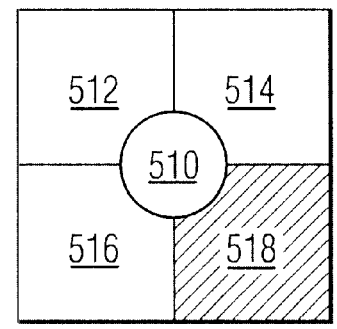
Figure 5G:
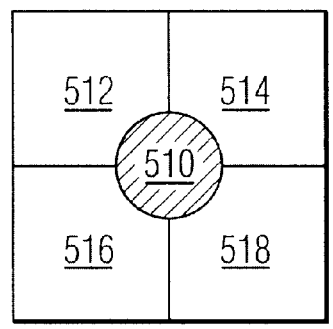
Figure 5H:
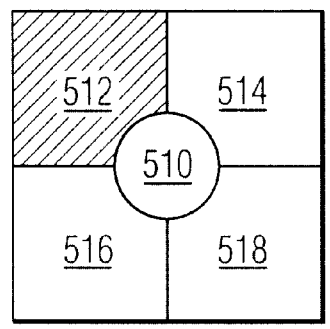
Figure 5I:
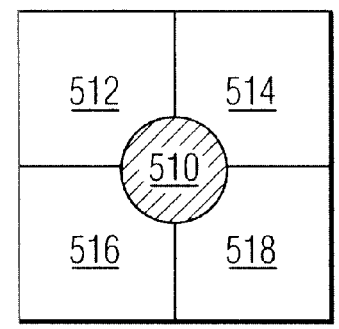

FIGS. 5a through 5i are diagrams of a transducer in operation in accordance with a third preferred embodiment of the present invention. Instead of a simple geometric division of the subject matter in the spot volume method, the sub-volumes include a region of interest, such as a heart valve. In this case, the process of obtaining the sub-frames is modified to acquire the region of interest on an more frequent basis, such as every other scan frame. n the example shown in FIG. 1, an area 510 has as been defined as a region of interest (ROI) and will be scanned every other cardiac cycle. Thus the sequence of scanning is: ROI 510 (FIG. 5a); lower left 516 (FIG. 5b); ROI 510 (FIG. 5c); upper right 514 (FIG. 5d); ROI 510 (FIG. 5e); lower right 518 (FIG. 5f); ROI 510 (FIG. 5g); upper left 512 (FIG. 5h); ROI 510 (FIG. 5i), etc. . . This sequence provide a clearer picture of the ROI 510 while sacrificing the scan rate of the remaining regions. This sequence would be an ideal candidate for the use of interpolation to smooth the transitions in the outside areas 512–518.

Figure 6A:
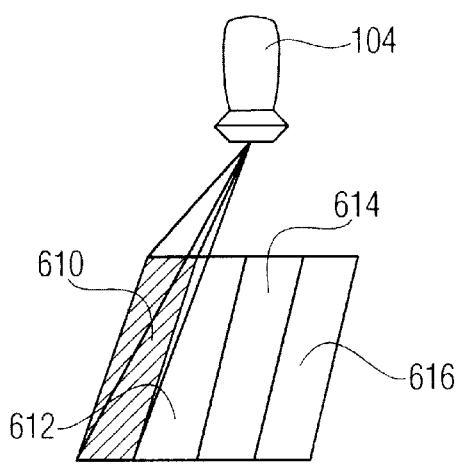
FIGS. 6a through 6e are diagrams of a transducer in operation in accordance with a fourth preferred embodiment of the present invention.
Figure 6B:
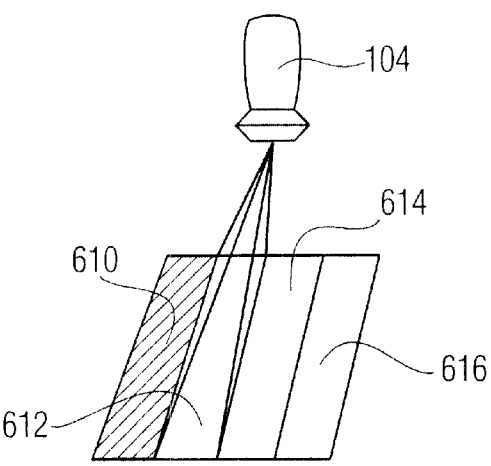
Figure 6C:
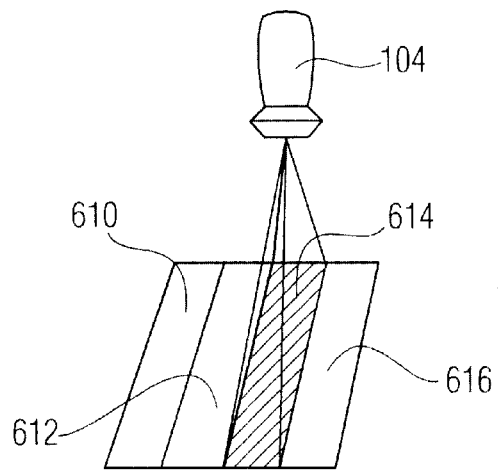
Figure 6D:
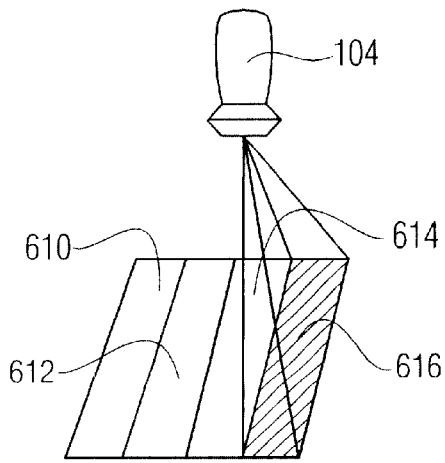
Figure 6E:
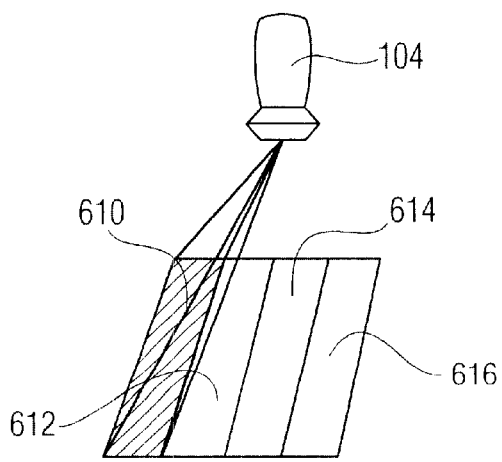

FIGS. 6a through 6e are diagrams of a transducer in operation in accordance with a fourth preferred embodiment of the present invention. In accordance with the fourth preferred embodiment, the volume to be imaged is divided into vertical (or horizontal depending on your orientation) slices to form the sub-volumes. In the example shown in FIGS. 6a through 6e, vertical slices 610, 612, 613, and 614 are defined for a volume. The sequence of scanning is: sub-volume 610 (FIG. 6a); sub-volume 612 (FIG. 6b); sub-volume 614 (FIG. 6c); and sub-volume 616 (FIG. 6d). The next series begins again at sub-volume 610 (FIG. 6e). This embodiment minimizes the discontinuities as between adjacent sub-volumes. Using four (4) vertical slices only creates three (3) areas of discontinuity at the interface between adjacent sub-volumes. More importantly, the temporal difference from one sub-volume to the next sub-volume is limited to a single cardiac cycle. Compare the configuration shown in FIGS. 3a–3e wherein four (4) areas of discontinuity exist with the maximum temporal difference being three (3) cardiac cycles between sub-volume 316 and sub-volume 310.

Although a few preferred embodiments of the present invention have been shown and described, it will be appreciated by those skilled in the art that changes may be made in these embodiments without departing from the principles and spirit of the invention, the scope of which is defined in the claims and their equivalents. For example, those of ordinary skill in the art will recognize that interleaving could be performed on data produced by a 1-D array. In such a case the 1-D array could be configured, for example to scan a ⅓ sweep each frame.

What is claimed is:

1. An ultrasound imaging system comprising:

a transducer that outputs and receives ultrasonic signals; and circuitry that causes the transducer to output the ultrasonic signals in a series of frames in an interleaved manner, each frame directed towards a different one of a plurality of portions of a subject matter, so as to insonify each of the plurality of portions of the subject matter at different times, and interleaves the received ultrasonic signals so as to form a composite image based on the echoes from a plurality of frames, and updates the composite image by updating each of the plurality of frames at different times.

2. An ultrasound system, as set forth in claim 1, wherein the circuitry causes the transducer to output the ultrasonic signals in an interleaved manner using a spot volume method, wherein said frames are arranged to cover successive portions of the subject matter that are generally contiguous with each other.

3. An ultrasound system, as set forth in claim 1, wherein the circuitry causes the transducer to output the ultrasonic signals in an interleaved manner using a sparse volume method, wherein said frames are arranged to cover successive portions of the subject matter that are generally non-contiguous with each other.

4. An ultrasound system, as set forth in claim 1, wherein the transducer comprises a two-dimensional array of elements capable of steering an ultrasonic beam in an azimuth and an elevation direction.

5. An ultrasound system, as set forth in claim 1, wherein the circuitry comprises:
  transmit circuitry that causes the transducer to output the ultrasonic signals in an interleaved manner;
  receive circuitry that receives echoes of the ultrasonic signals and transfers electrical signals representing the echoes into a memory based on the direction of the ultrasonic signal producing the echo thereby forming a complete set of ultrasound data based on the echoes from a number of frames equal to the number of plurality of portions; and
  display circuitry that displays an image based upon the ultrasound data in the memory.

6. An ultrasound system, as set forth in claim 5, wherein the circuitry further comprises:
  scan conversion circuitry that converts the ultrasound data in the memory into image data having X-Y coordinates for display by the display circuitry.

7. An ultrasound system, as set forth in claim 5, wherein the display circuitry further comprises:
  an interpolator that produces interpolated data for portions of the image data that have not been updated in a recent scan frame.

8. An ultrasound system, as set forth in claim 5, wherein the display circuitry further comprises:
  an alignment corrector that aligns image data from sequential frames.

9. An ultrasound imaging system comprising:
  a transducer that receives ultrasonic echoes and outputs electrical signals based thereon;
  a transmit circuit that causes the transducer to receive the ultrasonic echoes in an interleaved manner so as to scan different portions of a subject matter being imaged in different frames;
  a beamformer that delays and sums the electrical signals to produce echo data;
  a back-end that scan-converts the echo data into image data in a 2-D mode; and
  an image processor that, in a 3-D mode, combines the image data from a plurality of frames to create display data from which a subsequent composite image is presented to the user of the ultrasound system.

10. An ultrasound imaging system, as set forth in claim 9, wherein the image processor comprises:
  a processor unit; and
  a memory storing instructions and data for configuring the processor unit to combine the image data from different frames to create the display data.

11. An ultrasound imaging system, as set forth in claim 10, wherein the memory contains a instructions and data for configuring the processor unit to align image data from different frames.

12. An ultrasound imaging system, as set forth in claim 10, wherein the memory contains a instructions and data for configuring the processor unit to update image data by interpolation.

13. An ultrasound system, as set forth in claim 10, wherein the transducer comprises a two-dimensional array of elements capable of isonifying a volume.

14. A method of forming an ultrasound image comprising:
  identifying a region to be imaged;
  outputting ultrasonic signals over a first portion of the region to be imaged in a first frame by steering an ultrasonic beam along an azimuth and an elevation;
  receiving echoes from the first portion;
  outputting ultrasonic signals over a second portion of the region to be imaged in a second frame by steering an ultrasonic beam along an azimuth and an elevation;
  receiving echoes from the second portion; and
  combining data representing the echoes from the first and second portions.

15. A method of forming an ultrasound image comprising:
  identifying a region to be imaged;
  outputting ultrasonic signals over a first quarter of the region to be imaged in a first frame;
  receiving echoes from the first quarter;
  outputting ultrasonic signals over a second quarter of the region to be imaged in a second frame;
  receiving echoes from the second quarter;
  outputting ultrasonic signals over a third quarter of the region to be imaged in a third frame;
  receiving echoes from the third quarter;
  outputting ultrasonic signals over a fourth quarter of the region to be imaged in a fourth frame;
  receiving echoes from the fourth quarter; and
  combining data representing the echoes from the first, second, third, and fourth quarters to create an image of the region.

16. A method of forming an ultrasound image comprising:
  identifying a region to be imaged;
  identifying a plurality of sub-regions within the region;
  in a series of frames imaging the plurality of sub-regions, each sub-region being imaged for a cardiac cycle, and
  combining the images for plurality of sub-regions to produce an image of the region.

17. An ultrasound imaging system comprising:
  a transducer that outputs and receives ultrasonic signals; and
  circuitry that causes the transducer to output the ultrasonic signals so as to image a series of sub-volumes, one sub-volume for each of a predetermined number of cardiac cycles of a patient, and forms an image based on the echoes from the sub-volumes.

18. An add-on upgrade to an ultrasound system comprising:
   a channel link that obtains echo data from a back-end of the ultrasound system;
   a processor; and
   a memory that contains programs to configure the processor so as to:
      control the channel link to obtain 3D echo data; and
      process the 3D echo data so as to create data that can be displayed on a monitor.

* * * * *